United States Patent
Yamada et al.

(10) Patent No.: US 12,357,231 B2
(45) Date of Patent: Jul. 15, 2025

(54) PAIN EVALUATION DEVICE, PAIN EVALUATION METHOD, AND NON-TRANSITORY STORAGE MEDIUM STORING PAIN EVALUATION PROGRAM

(71) Applicant: OMRON HEALTHCARE Co., Ltd., Kyoto (JP)

(72) Inventors: Keisuke Yamada, Kyoto (JP); Mitsuru Samejima, Kyoto (JP); Tamaki Ito, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 808 days.

(21) Appl. No.: 17/447,135

(22) Filed: Sep. 8, 2021

(65) Prior Publication Data

US 2021/0393195 A1 Dec. 23, 2021

Related U.S. Application Data

(63) Continuation of application No. PCT/JP2020/006648, filed on Feb. 19, 2020.

(30) Foreign Application Priority Data

Mar. 13, 2019 (JP) .................... 2019-045936

(51) Int. Cl.
*A61B 5/00* (2006.01)
*A61B 5/024* (2006.01)
(Continued)

(52) U.S. Cl.
CPC ........ *A61B 5/4824* (2013.01); *A61B 5/02405* (2013.01); *A61B 5/352* (2021.01);
(Continued)

(58) Field of Classification Search
None
See application file for complete search history.

(56) References Cited

U.S. PATENT DOCUMENTS 4,505,278 A * 3/1985 Alban .................. A61B 5/4824
600/587
4,641,661 A * 2/1987 Kalarickal ........... A61B 5/4824
600/557
(Continued)

FOREIGN PATENT DOCUMENTS

CN 102065756 A 5/2011
CN 107320073 A 11/2017
(Continued)

OTHER PUBLICATIONS

Chuang et al., 2007, "Pain assessment in musculoskeletal pain patients by heart rate variability", Journal of Musculoskeletal Pain, 15(4), 67-74. (Year: 2007).*

(Continued)

*Primary Examiner* — Michael R Bloch
(74) *Attorney, Agent, or Firm* — Birch, Stewart, Kolasch & Birch, LLP

(57) ABSTRACT

To provide a pain evaluation device, a pain evaluation method, and a non-transitory storage medium storing a pain evaluation program that can evaluate the degree of pain in each individual. A control unit includes: an electrocardiographic waveform acquisition unit configured to acquire electrocardiographic waveform data of a user; and a pain determination unit configured to determine, based on a comparison between first electrocardiographic waveform data obtained by the electrocardiographic waveform acquisition unit in a state where no physical load is applied to the body of the user and second electrocardiographic waveform data obtained by the electrocardiographic waveform acqui- (Continued)

sition unit in a state where a load is applied to the body of the user, a degree of pain sensed by the user in a state where the load is applied.

11 Claims, 8 Drawing Sheets

(51) Int. Cl.
*A61B 5/352* (2021.01)
*A61B 5/353* (2021.01)

(52) U.S. Cl.
CPC ............ *A61B 5/7246* (2013.01); *A61B 5/024* (2013.01); *A61B 5/353* (2021.01)

(56) References Cited

U.S. PATENT DOCUMENTS

| | | | | |
|---|---|---|---|---|
| 5,906,583 | A * | 5/1999 | Rogel | A61B 5/6841 600/515 |
| 6,315,736 | B1 * | 11/2001 | Tsutsumi | A61B 5/1106 600/587 |
| 8,512,240 | B1 * | 8/2013 | Zuckerman-Stark | A61B 5/0261 128/924 |
| 2004/0019289 | A1 * | 1/2004 | Ross | A61B 5/02405 600/519 |
| 2004/0019303 | A1 * | 1/2004 | Thomson | A61B 5/4824 600/595 |
| 2005/0272984 | A1 * | 12/2005 | Huiku | A61B 5/4824 600/521 |
| 2006/0052720 | A1 * | 3/2006 | Ross | A61B 5/00 600/595 |
| 2006/0052729 | A1 * | 3/2006 | Gurses | A61H 23/02 600/557 |
| 2008/0132801 | A1 * | 6/2008 | Logier | A61B 5/352 600/523 |
| 2011/0082384 | A1 | 4/2011 | Harte et al. | |
| 2011/0112420 | A1 | 5/2011 | Nagata et al. | |
| 2014/0276549 | A1 * | 9/2014 | Osorio | A61B 5/165 604/503 |
| 2015/0025334 | A1 * | 1/2015 | Jain | A61B 5/7246 600/323 |
| 2015/0025335 | A1 * | 1/2015 | Jain | A61B 5/1102 600/509 |
| 2016/0213314 | A1 * | 7/2016 | Zuckerman-Stark | A61B 5/7264 |
| 2017/0136265 | A1 * | 5/2017 | Hyde | A61N 7/00 |
| 2018/0085055 | A1 * | 3/2018 | Annoni | A61B 5/4824 |

FOREIGN PATENT DOCUMENTS

| | | |
|---|---|---|
| JP | 2005-000409 A | 1/2005 |
| JP | 2005-040187 A | 2/2005 |
| JP | 2008-513073 A | 5/2008 |
| JP | 2009-261779 A | 11/2009 |
| JP | 2016-22335 A | 2/2016 |
| JP | 2019-93095 A | 6/2019 |
| WO | 2009/157185 A1 | 12/2009 |
| WO | 2017/157746 A1 | 9/2017 |

OTHER PUBLICATIONS

International Preliminary Report on Patentability for International Application No. PCT/JP2020/006648, dated Dec. 16, 2020.
International Search Report for International Application No. PCT/JP2020/006648, Dated Apr. 21, 2020.
Akiyama, Yoko, "Development of an Objective Evaluation System of Somatic Sensations Using Biomedical Signals", Tateisi Science and Technology Foundation, Grant-Supported Research Results Report, 2011, vol. 20, pp. 51-55.
Chinese Office Action and Search Report for Chinese Application No. 202080018075.6, dated Oct. 28, 2023, with an English translation.

* cited by examiner

PAIN EVALUATION DEVICE, PAIN EVALUATION METHOD, AND NON-TRANSITORY STORAGE MEDIUM STORING PAIN EVALUATION PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2020/006648, filed Feb. 19, 2020, which application claims priority to Japanese Patent Application No. 2019-045936, filed Mar. 13, 2019, which applications are incorporated herein by reference in their entireties.

TECHNICAL FIELD

The present invention relates to a pain evaluation device, a pain evaluation method, and a non-transitory storage medium storing a pain evaluation program.

BACKGROUND ART

A portable electrocardiograph that is the type routinely carried by a user is known (see Patent Documents 1 and 2). In addition, the knowledge that pain evaluation can be performed by heart rate variability analysis (specifically, frequency analysis) is described in Non-patent Literature 1.

CITATION LIST

Patent Literature

Patent Document 1: JP 2005-000409 A
Patent Document 2: JP 2005-040187 A

NON-PATENT LITERATURE

Non-patent Literature 1: Tateisi Science and Technology Foundation, Report of granted research (No. 20), 2011, 51 page to 55 page: "Development of Objective Evaluation System using Biological Signals for Somesthetic Sense"

SUMMARY OF INVENTION

Technical Problem

Non-patent Literature 1 describes that periodic variations in RR interval that is an interval between R-waves each of which is the maximum amplitude of an electrocardiographic waveform are correlated with pain. However, absolute evaluation of pain is performed in Non-patent Literature. How pain is sensed differs among individuals, and only observation of the periodic variations in RR interval cannot tell the degree of pain in each individual.

An object of the present invention is to provide a pain evaluation device, a pain evaluation method, and a computer-readble storage medium storing a pain evaluation program that can evaluate the degree of pain in each individual.

Solution to Problem

According to a first aspect of the present invention, a pain evaluation device (for example, a control unit 21 in the following embodiment) for evaluating pain of a user, the pain evaluation device including:

an electrocardiographic waveform acquisition unit configured to acquire electrocardiographic waveform data of the user; and a pain determination unit configured to determine, based on a comparison between first electrocardiographic waveform data obtained by the electrocardiographic waveform acquisition unit in a state where no physical load is applied to the body of the user and second electrocardiographic waveform data obtained by the electrocardiographic waveform acquisition unit in a state where a load is applied to the body of the user, a degree of pain sensed by the user in a state where the load is applied.

According to the first aspect, the degree of pain is determined based on a comparison between the first electrocardiographic waveform data in a state where no physical load is applied to the body of the user and the second electrocardiographic waveform data obtained in a state where a physical load is applied to the body of the user. Therefore, how differently pain is sensed by each user can be, for example, quantified, which can help diagnosis by a physician, treatment of a painful site, or the like.

According to a second aspect of the present invention, in the pain evaluation device described in the first aspect, the pain determination unit determines the degree of pain based on a difference or ratio between a PP interval or an RR interval obtained from two adjacent electrocardiographic waveforms based on the first electrocardiographic waveform data and a PP interval or an RR interval obtained from two adjacent electrocardiographic waveforms based on the second electrocardiographic waveform data.

According to the second aspect, determination of the degree of pain can be performed by simple processing.

According to a third aspect of the present invention, in the pain evaluation device described in the second aspect, when an absolute value of the difference exceeds a threshold, the pain determination unit determines that the degree of pain is larger than that when the absolute value is at the threshold or lower.

According to the third aspect, determination of the degree of pain can be performed by simple processing.

According to a fourth aspect of the present invention, the pain evaluation device described in the second aspect, when a difference between the ratio and a reference value exceeds a threshold, the pain determination unit determines that the degree of pain is larger than that when the difference is at the threshold or lower.

According to the fourth aspect, determination of the degree of pain can be performed by simple processing.

According to a fifth aspect of the present invention, in the pain evaluation device described in the second aspect, the pain determination unit calculates the difference for each of the first electrocardiographic waveform data and the second electrocardiographic waveform data that are obtained at different timings, and determines the degree of pain based on a plurality of the differences.

According to the fifth aspect, the degree of pain is determined based on the plurality of the differences; therefore, determination accuracy can be increased.

According to a sixth aspect of the present invention, in the pain evaluation device described in the fifth aspect, when an average value of absolute values of the plurality of the differences exceeds a threshold, the pain determination unit determines that the degree of pain is larger than that when the average value is at the threshold or lower.

According to the sixth aspect, the degree of pain is determined based on the plurality of the differences; therefore, determination accuracy can be increased.

According to a seventh aspect of the present invention, in the pain evaluation device described in the second aspect, the pain determination unit calculates the ratio for each of the first electrocardiographic waveform data and the second electrocardiographic waveform data that are obtained at different timings, and determines the degree of pain based on a plurality of the ratios.

According to the seventh aspect, the degree of pain is determined based on the plurality of the ratios; therefore, determination accuracy can be increased.

According to an eighth aspect of the present invention, in the pain evaluation device described in the seventh aspect, when a difference between an average value of the plurality of the ratios and a reference value exceeds a threshold, the pain determination unit determines that the degree of pain is larger than that when the average value is at the threshold or lower.

According to the eighth aspect, the degree of pain is determined based on the plurality of the ratios; therefore, determination accuracy can be increased.

According to a ninth aspect of the present invention, in the pain evaluation device described any one of the second to eighth aspects, the pain determination unit calculates, as the ratio or the difference, a ratio or difference between an average value of a plurality of the PP intervals based on the first electrocardiographic waveform data or an average value of a plurality of the RR intervals based on the first electrocardiographic waveform data, and an average value of a plurality of the PP intervals based on the second electrocardiographic waveform data or an average value of a plurality of the RR intervals based on the second electrocardiographic waveform data.

According to the ninth aspect, the influence of variations in the PP interval or the RR interval can be eliminated; therefore, accuracy of determining the degree of pain can be increased.

According to a tenth aspect of the present invention, in the pain evaluation device described in any one of the first to ninth aspects, the load applied to the body of the user is generated by a dedicated device.

According to the tenth aspect, the second electrocardiographic waveform data can be acquired in a state where a certain load is applied to the user by the dedicated device. Therefore, variations in application of the load to the affected area with injury can be eliminated for example, and the degree of pain in the affected area can be determined with high accuracy.

According to an eleventh aspect of the present invention, a pain evaluation method of evaluating pain of a user, the pain evaluation method including:

an electrocardiographic waveform data acquisition step of acquiring electrocardiographic waveform data of the user; and a pain determination step of determining, based on a comparison between first electrocardiographic waveform data obtained by the electrocardiographic waveform acquisition step in a state where no physical load is applied to the body of the user and second electrocardiographic waveform data obtained by the electrocardiographic waveform acquisition step in a state where a load is applied to the body of the user, a degree of pain sensed by the user in a state where the load is applied.

According to a twelfth aspect of the present invention, a computer-readble storage medium storing a pain evaluation program for evaluating pain of a user, the program allowing a computer to execute:

an electrocardiographic waveform data acquisition step of acquiring electrocardiographic waveform data of the user; and a pain determination step of determining, based on a comparison between first electrocardiographic waveform data obtained by the electrocardiographic waveform acquisition step in a state where no physical load is applied to the body of the user and second electrocardiographic waveform data obtained by the electrocardiographic waveform acquisition step in a state where a load is applied to the body of the user, a degree of pain sensed by the user in a state where the load is applied.

Advantageous Effects of Invention

According to an aspect of the present invention, a pain evaluation device, a pain evaluation method, and a computer-readble storage medium
storing a pain evaluation program that can evaluate the degree of pain in each individual can be provided.

DESCRIPTION OF EMBODIMENTS

Overview of Pain Evaluation System of Embodiment

A pain evaluation system according to an embodiment of the present invention is configured to determine, based on an electrocardiographic waveform of a user, the degree of pain sensed by the user. For example, in a user with a failure such as sprain, a state where a load is applied to the affected area, by pressing the affected area with a finger or in another manner, and a state where no load is applied to the affected area without touching the affected area are formed. The pain evaluation system acquires electrocardiographic waveform data (data containing electrocardiographic waveforms of at least two beats) of the user measured with an electrocardiograph in these two states. The pain evaluation system obtains an RR interval, which is an interval between R waves in two electrocardiographic waveforms adjacent to each other (or a PP interval, which is an interval between P waves), from each of the two pieces of electrocardiographic waveform data, and determines, based on a comparison between the two RR intervals (or the PP intervals), the degree of pain sensed by the user in a state where a load is applied to the affected area.

The inventors have found that a difference between the RR intervals (or the PP intervals) is generated between a state where no load is applied to the affected area and a state where a load is applied to the affected area, and on the basis of such finding, succeeded in scoring the degree of pain from the magnitude of a difference or ratio between the RR intervals (or the PP intervals) in each of the two states. How pain is sensed differs from users; however, with this method, a user can know, from the magnitude of a difference or a ratio between two RR intervals (or PP intervals) acquired from an identical user, how much pain in the affected area has changed (ameliorated or deteriorated).

Concrete Configuration of Pain Evaluation System of Embodiment

Figure 1:
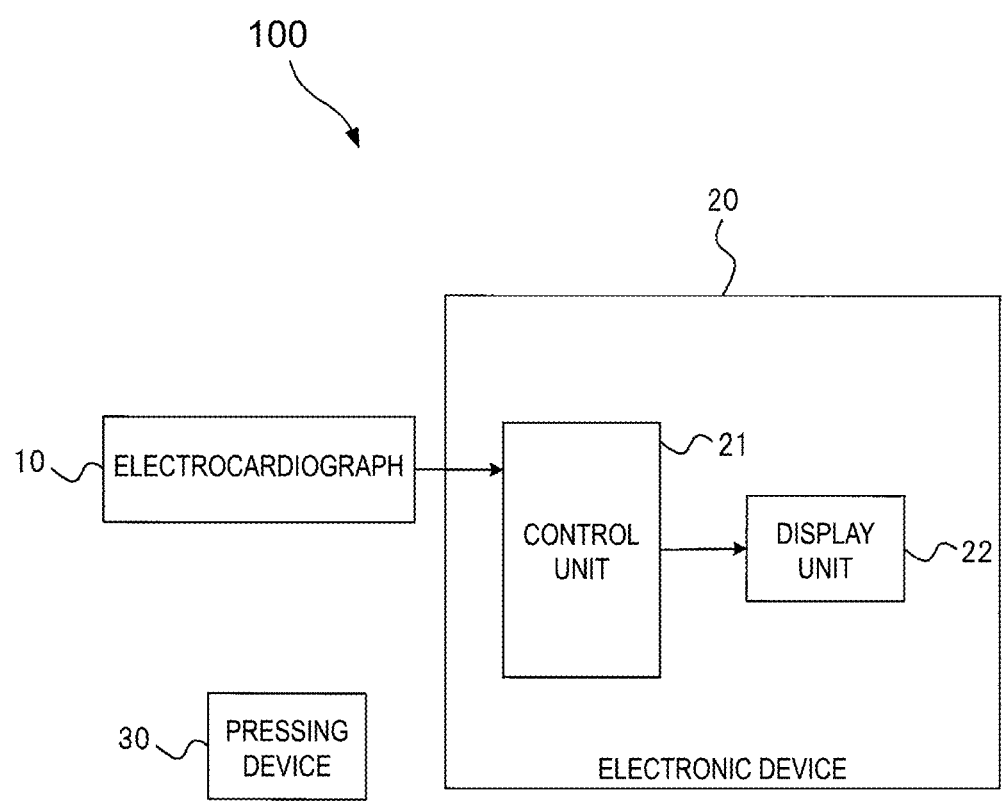
FIG. 1 is a schematic view illustrating an overall configuration of a pain evaluation system 100.

FIG. 1 is a schematic view illustrating an overall configuration of the pain evaluation system 100. The pain evaluation system 100 illustrated in FIG. 1 includes an electrocardiograph 10, the electronic device 20, and a pressing device 30.

The electrocardiograph 10 serves to measure an electrocardiographic waveform of a user, and for example, the electrocardiograph described in Patent Documents 1, 2 is applied.

The electronic device 20 is, for example, a smartphone, a tablet-type device, a personal computer, or the like. Specifically, the electronic device 20 includes the control unit 21, a display unit 22, and a communication interface (not illustrated) for connecting to the electrocardiograph 10 and the pressing device 30. The electrocardiograph 10 and the electronic device 20 are configured so as to communicate via wired communication or wireless communication. The electrocardiographic waveform data (aggregation of electrocardiographic waveforms of one beat) of a user measured by the electrocardiograph 10 is transmitted via the communication interface to the electronic device 20.

The control unit 21 includes a central processing unit (CPU), a random access memory (RAM), a read only memory (ROM), and the like and performs integrated control or the like of the electronic device 20 in accordance with programs. Programs including a pain evaluation program are stored in the ROM of the control unit 21.

The display unit 22 is a device such as a liquid crystal display panel or an organic EL (electro-luminescence) display panel capable of displaying an image.

The pressing device 30 is a device for applying a physical load (that is, stimulus) to a particular location (for example, the affected area with pain) of the body of the user. Specifically, the pressing device 30 includes a rod-shaped member, a movement mechanism that allows the rod-shaped member to move in the longitudinal direction, an operation member for operating the movement mechanism, and a communication interface for communicating with the electronic device 20.

The user presses a protruding opening of the rod-shaped member of the pressing device 30 against the affected area and operates the operation member to perform operation for making the rod-shaped member protrude from the protruding opening by using the movement mechanism. This operation brings a tip end of the rod-shaped member protruding from the protruding opening to be pressed against the affected area of the user with a certain force, and thus a physical load is applied to the affected area. When the rod-shaped member is driven as just described, information indicating that a load is applied to the user is transmitted from the pressing device 30 to the electronic device 20. When the rod-shaped member is not driven, information indicating that no load is applied to the user is transmitted from the pressing device 30 to the electronic device 20.

Function of Control Unit 21

Figure 2:
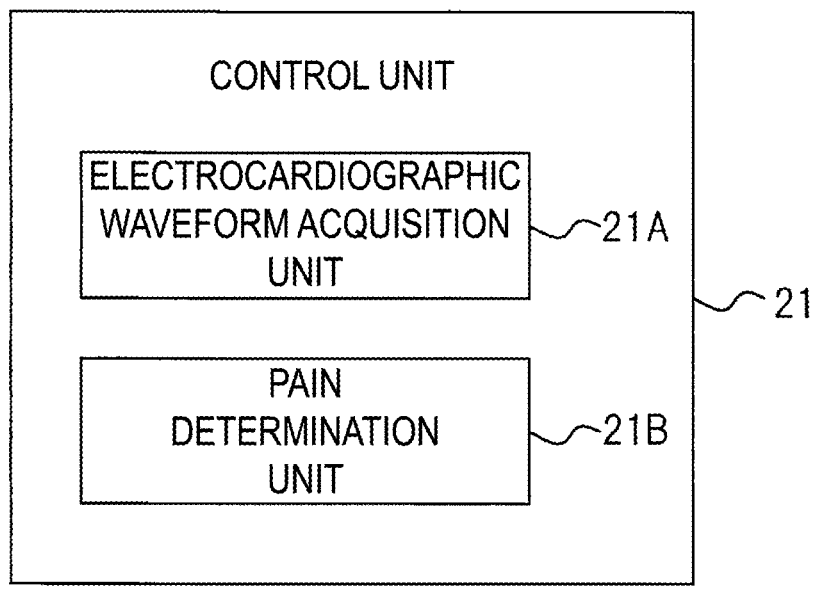
FIG. 2 is a diagram illustrating a functional block of a control unit 21 of the pain evaluation system 100 illustrated in FIG. 1.

FIG. 2 is a diagram illustrating a functional block of the control unit 21 of the pain evaluation system 100 illustrated in FIG. 1. The CPU of the control unit 21 executes the aforementioned pain evaluation program stored in the ROM and thereby functions as an electrocardiographic waveform acquisition unit 21A and a pain determination unit 21B.

The electrocardiographic waveform acquisition unit 21A acquires electrocardiographic waveform data of the user measured by the electrocardiograph 10.

The pain determination unit 21B determines, based on a comparison between: first electrocardiographic waveform data acquired by the electrocardiographic waveform acquisition unit 21A in a state where no load is applied to the body of the user by the pressing device 30; and second electrocardiographic waveform data acquired by the electrocardiographic waveform acquisition unit 21A in a state where a load is applied to the body of the user by the pressing device 30, the degree of pain sensed by the user in a state where a load is applied by the pressing device 30. The pain determination unit 21B, for example, scores the determined degree of pain, allows the score to be displayed on the display unit 22 or output from a speaker (not illustrated), and thereby notifies the user or medical professionals who perform treatment.

Figure 3:
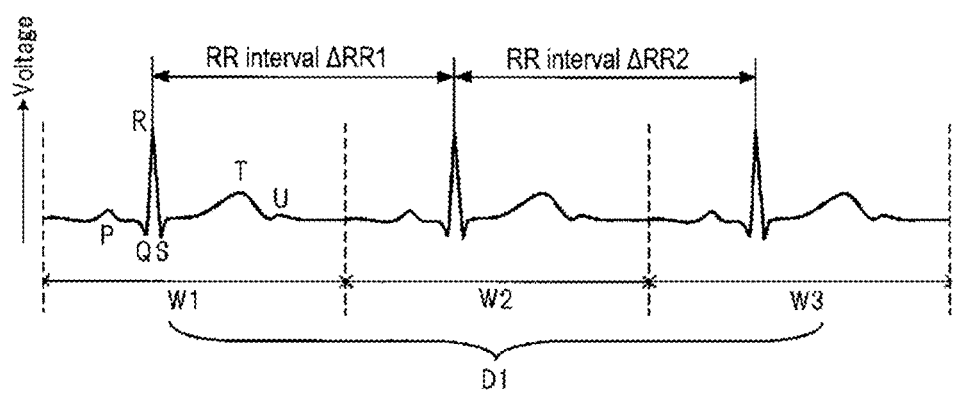
FIG. 3 is a diagram illustrating one example of first electrocardiographic waveform data.

FIG. 3 is a diagram illustrating an example of the first electrocardiographic waveform data. A first electrocardiographic waveform data D1 illustrated in FIG. 3 includes three continuous electrocardiographic waveforms (electrocardiographic waveform W1, electrocardiographic waveform W2, and electrocardiographic waveform W3). Each of the electrocardiographic waveforms is formed of P, Q, R, S, T, and U waves. The pain determination unit 21B calculates at least one interval between the R waves of the two adjacent electrocardiographic waveforms in the first electrocardiographic waveform data D1. FIG. 3 illustrates an example in which two RR intervals are calculated, the RR intervals being: an RR interval $\Delta RR1$ that is an interval between the R wave of the electrocardiographic waveform W1 and the R wave of the electrocardiographic waveform W2; and an RR interval $\Delta RR2$ that is an interval between the R wave of the electrocardiographic waveform W2 and the R wave of the electrocardiographic waveform W3.

Figure 4:
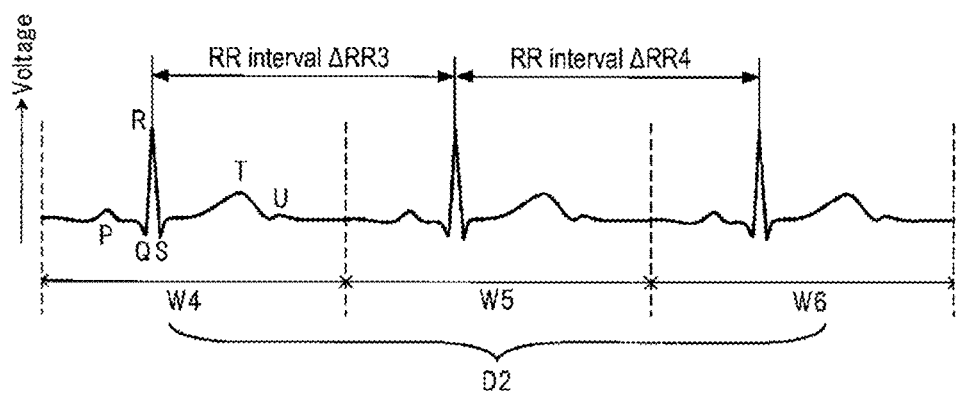
FIG. 4 is a diagram illustrating one example of second electrocardiographic waveform data.

FIG. 4 is a diagram illustrating one example of the second electrocardiographic waveform data. A second electrocardiographic waveform data D2 illustrated in FIG. 4 includes three continuous electrocardiographic waveforms (electrocardiographic waveform W4, electrocardiographic waveform W5, and electrocardiographic waveform W6). Each of the electrocardiographic waveforms is formed of P, Q, R, S, T, and U waves. The pain determination unit 21B calculates at least one interval between the R waves of the two adjacent electrocardiographic waveforms in the second electrocardiographic waveform data D2. FIG. 4 illustrates an example in which two RR intervals are calculated, the RR intervals being: an RR interval $\Delta RR3$ that is an interval between the R wave of the electrocardiographic waveform W4 and the R wave of the electrocardiographic waveform W5; and an RR interval $\Delta RR4$ that is an interval between the R wave of the electrocardiographic waveform W5 and the R wave of the electrocardiographic waveform W6.

The pain determination unit 21B determines the degree of pain of the user by comparing the RR interval in the first electrocardiographic waveform data D1 with the RR interval in the second electrocardiographic waveform data D2 calculated as described above.

Specific Example of Pain Determination Method

Figure 5:
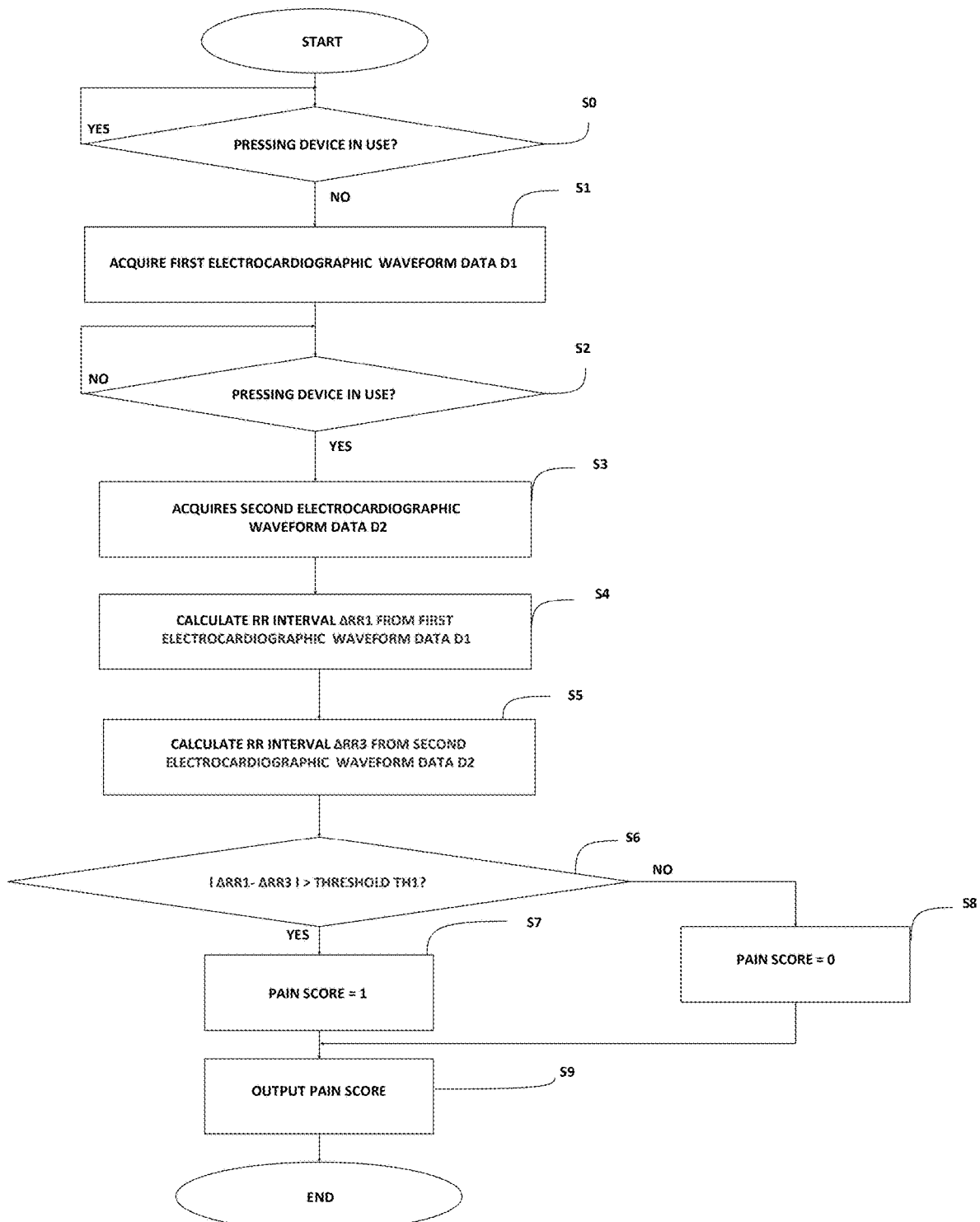
FIG. 5 is a flowchart for illustrating the operation of the control unit 21 of an electronic device 20 illustrated in FIG. 1.

FIG. 5 is a flowchart for illustrating the operation of the control unit 21 of the electronic device 20 illustrated in FIG. 1. The electrocardiographic waveform acquisition unit 21A of the control unit 21 determines based on the content of information received from the pressing device 30 whether the pressing device 30 is in use (a state where a physical load is applied to the body of the user) (step S0).

In a case determining that the pressing device 30 is not in use (step S0: NO), the electrocardiographic waveform acquisition unit 21A acquires the first electrocardiographic waveform data D1 illustrated in FIG. 3 from the electrocardiograph 10 and stores the first electrocardiographic waveform data D1 in the RAM (step S1).

Next, the electrocardiographic waveform acquisition unit 21A determines based on the content of information received from the pressing device 30 whether the pressing device 30 is in use (step S2). In a case determining that the pressing device 30 is in use (step S2: YES), the electrocardiographic waveform acquisition unit 21A acquires the second electrocardiographic waveform data D2 illustrated in FIG. 4 from the electrocardiograph 10 and stores the second electrocardiographic waveform data D2 in the RAM (step S3).

Next, the pain determination unit 21B calculates one RR interval (here, the RR interval ΔRR1) from the first electrocardiographic waveform data D1 acquired in step S1 (step S4), and calculates one RR interval (here, the RR interval ΔRR3) from the second electrocardiographic waveform data D2 acquired in step S3 (step S5).

Next, the pain determination unit 21B calculates an absolute value of a difference between the RR interval ΔRR1 calculated in step S4 and the RR interval ΔRR3 calculated in step S5, and determines whether the absolute value exceeds a predetermined threshold TH1 (step S6).

The difference between the RR interval ΔRR1 and the RR interval ΔRR3 is zero except for a measurement error of each of the RR intervals and variations in the RR interval of the user as long as there is little pain in the affected area. The threshold TH1 is set to a value obtained by adding, to zero, a value determined based on a measurement error of the RR interval measured by the electrocardiograph 10 and variations in the RR interval of the user. As a result, when the aforementioned absolute value exceeds the threshold TH1, it can be determined that a change in the RR interval due to pain is generated, and when the aforementioned absolute value is at the threshold TH1 or lower, it can be determined that a change in the RR interval due to pain is not generated.

When the absolute value exceeds the threshold TH1 (step S6: YES), the pain determination unit 21B determines a pain score indicating the degree of pain as "1" for example (a numerical value indicating that there is pain) (step S7). Meanwhile, when the absolute value is at the threshold TH1 or lower (step S6: NO), the pain determination unit 21B determines a pain score indicating the degree of pain as "0" for example (a numerical value indicating that there is no pain) (step S8). Here, the pain score is a value for evaluating pain at two levels with pain or without pain; however, the threshold TH1 may be set to multiple levels such that each time the aforementioned absolute value exceeds the threshold for each level, the pain score increases in a stepwise manner.

When the pain determination unit 21B determines the pain score, the pain determination unit 21B displays the determined pain score on the display unit 22 and notifies the user or others (step S9).

Effects of Pain Evaluation System of Embodiment

As described above, according to the pain evaluation system 100, the degree of pain is determined based on a difference between: an RR interval obtained from the first electrocardiographic waveform data in a state where a physical load is not applied to the body; and an RR interval obtained from the second electrocardiographic waveform data in a state when a physical load is applied to the body. The difference is close to zero when pain is mild, and is away from zero when pain is severe. Therefore, the difference is checked, and thus information, for example, whether pain is mitigated or whether pain is increased can be judged. As a result, it can help diagnosis by a physician, treatment of a painful site, or the like.

Additionally, in FIG. 5, an average of the RR interval ΔRR1 and the RR interval ΔRR2 (or an average of three or more RR intervals obtained from the first electrocardiographic waveform data) may be calculated in step S4, and an average of the RR interval ΔRR3 and the RR interval ΔRR4 (or an average of three or more RR intervals obtained from the second electrocardiographic waveform data) may be calculated in step S5. In this case, a value compared with the threshold TH1 in step S6 is preferably an absolute value of a difference between the two average values. Such setting can eliminate influence due to variations in the RR interval and can improve accuracy of determining pain.

Moreover, in a case where multiple RR intervals are calculated in each of steps S4 and S5 as just described, variations (dispersions) of all of the RR intervals obtained from the first electrocardiographic waveform data and variations (dispersions) of all of the RR intervals obtained from the second electrocardiographic waveform data are calculated, and in a case where any of the two dispersions is at the threshold or higher, it is determined that the pain determination cannot be made and then processing after step S6 may not be performed. When the variation in the RR interval is large, accuracy of determining the degree of pain in step S6 may decrease. Accordingly, the pain determination cannot be made when the variation is large, and thus an erroneous determination of the degree of pain can be prevented.

First Modified Example of Specific Example of Pain Determination Method

Figure 6:
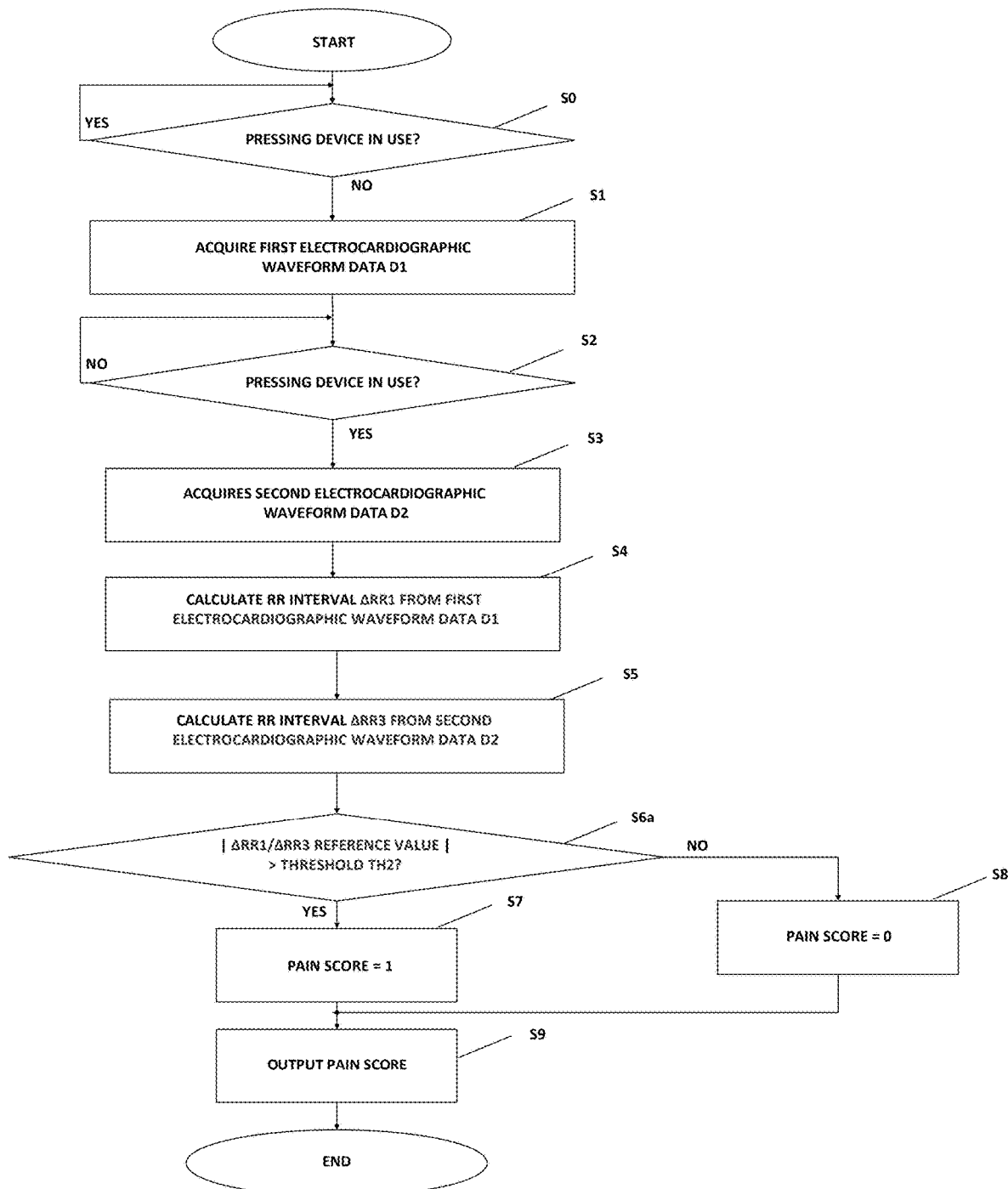
FIG. 6 is a flowchart for illustrating a first modified example of the operation of the control unit 21 of the electronic device 20 illustrated in FIG. 1.

FIG. 6 is a flowchart for illustrating a first modified example of the operation of the control unit 21 of the electronic device 20 illustrated in FIG. 1. The flowchart illustrated in FIG. 6 is identical to FIG. 5 except that step S6 is changed to step S6a. In FIG. 6, the identical processing as that in FIG. 5 is assigned with the identical reference sign and the description thereof is omitted.

After step S5, the pain determination unit 21B calculates a ratio (ΔRR1/ΔRR3) between the RR interval ΔRR1 calculated in step S4 and the RR interval ΔRR3 calculated in step S5, and determines whether an absolute value of a difference between the ratio and a predetermined reference value exceeds a predetermined threshold TH2 (step S6a).

The ratio between the RR interval ΔRR1 and the RR interval ΔRR3 is "1" except for a measurement error of each of the RR intervals and variations in the RR interval of the user as long as there is little pain in the affected area. The reference value is set to "1", and the threshold TH2 is set to a value obtained by adding, to zero, a value determined based on a measurement error of the RR interval measured by the electrocardiograph 10 and variations in the RR interval of the user. As a result, when the absolute value exceeds the threshold TH2, it can be determined that a change in the RR interval due to pain is generated, and when the aforementioned absolute value is at the threshold TH2 or lower, it can be determined that a change in the RR interval due to pain is not generated.

When the absolute value exceeds the threshold TH2 (step S6a: YES), the pain determination unit 21B determines a pain score indicating the degree of pain as "1" for example (a numerical value indicating that there is pain) (step S7). Meanwhile, when the absolute value is at the threshold TH2 or lower (step S6a: NO), the pain determination unit 21B determines a pain score indicating the degree of pain as "0" (a numerical value indicating that there is no pain) (step S8). Here, the pain score is a value for evaluating pain at two levels with pain or without pain; however, the threshold TH2 may be set to multiple levels such that each time the aforementioned absolute value exceeds the threshold for each level, the pain score increases in a stepwise manner.

As described above, according to the operation example illustrated in FIG. 6, the degree of pain is determined based on a ratio between an RR interval obtained from the first electrocardiographic waveform data in a state where a physical load is not applied to the body and an RR interval obtained from the second electrocardiographic waveform data in a state where a physical load is applied to the body. The ratio is close to 1 when pain is mild, and is away from 1 when pain is severe. Therefore, the ratio is checked, and thus information, for example, whether pain is mitigated or whether pain is increased can be judged. As a result, it can help diagnosis by a physician, treatment of a painful site, or the like.

Additionally, in FIG. 6, an average of the RR interval ΔRR1 and the RR interval ΔRR2 may be calculated in step S4, and an average of the RR interval ΔRR3 and the RR interval ΔRR4 may be calculated in step S5. In this case, a value compared with the threshold TH2 in step S6a is preferably an absolute value of a difference between a reference value and a ratio between the two average values. Such setting can eliminate influence due to variations in the RR interval and can improve accuracy of determining pain.

Second Modified Example of Specific Example of Pain Determination Method

Figure 7:
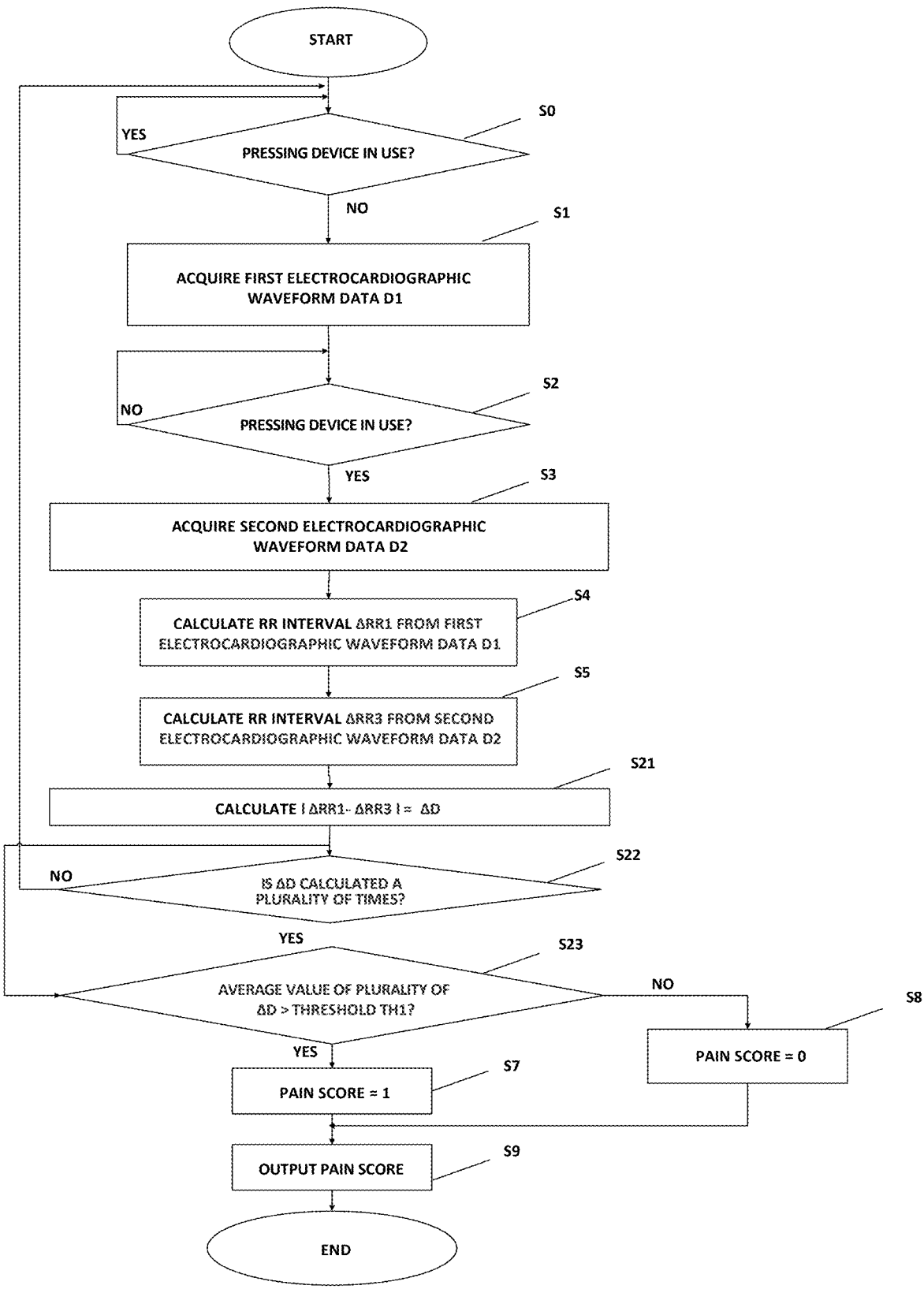
FIG. 7 is a flowchart for illustrating a second modified example of the operation of the control unit 21 of the electronic device 20 illustrated in FIG. 1.

FIG. 7 is a flowchart for illustrating a second modified example of the operation of the control unit 21 of the electronic device 20 illustrated in FIG. 1. The flowchart illustrated in FIG. 7 is identical to FIG. 5 except that step S6 is changed to step S21, step S22, and step S23. In FIG. 7, the identical processing as that in FIG. 5 is assigned with the identical reference sign and description thereof is omitted.

After step S5, the pain determination unit 21B calculates an absolute value ΔD of a difference between the RR interval ΔRR1 and the RR interval ΔRR3 (step S21). Thereafter, the pain determination unit 21B determines whether the absolute value ΔD is calculated a plurality of times (e.g., twice) (step S22). When the absolute value ΔD is not calculated twice (step S22: NO), the pain determination unit 21B shifts the processing to step S0. When the absolute value ΔD is calculated twice (step S22: YES), the pain determination unit 21B calculates an average value of the two absolute values ΔD and determines whether the average value exceeds the threshold TH1 (step S23).

When the average value exceeds the threshold TH1 (step S23: YES), the pain determination unit 21B performs the processing of step S7. When the average value is at the threshold TH1 or lower (step S23: NO), the pain determination unit 21B performs the processing of step S8.

As described above, according to the operation example illustrated in FIG. 7, the degree of pain is determined based on a plurality of differences (absolute values ΔD); therefore, determination accuracy can be increased.

Additionally, in step S23 of FIG. 7, the maximum and minimum values of the plurality of absolute values ΔD may be excluded, and an average value of the remaining absolute values ΔD may be calculated and the average value and the threshold TH1 may be compared. Alternatively, a median value of the plurality of absolute values ΔD may be compared with the threshold TH1. As a result, the influence of sudden noise or the like can be eliminated.

Moreover, in step S23 of FIG. 7, each of the plurality of absolute values ΔD is compared with the threshold TH1, and of the plurality of absolute values ΔD, the number of absolute values ΔD exceeding the threshold TH1 reaches the predetermined number of absolute values ΔD (one or more freely selected values). In such a case, the processing may be shifted to step S7. Of the plurality of absolute values ΔD, the number of absolute values ΔD exceeding the threshold TH1 does not reach the predetermined number of absolute values ΔD (one or more freely selected values). In such a case, the processing may be shifted to step S8.

Third Modified Example of Specific Example of Pain Determination Method

Figure 8:
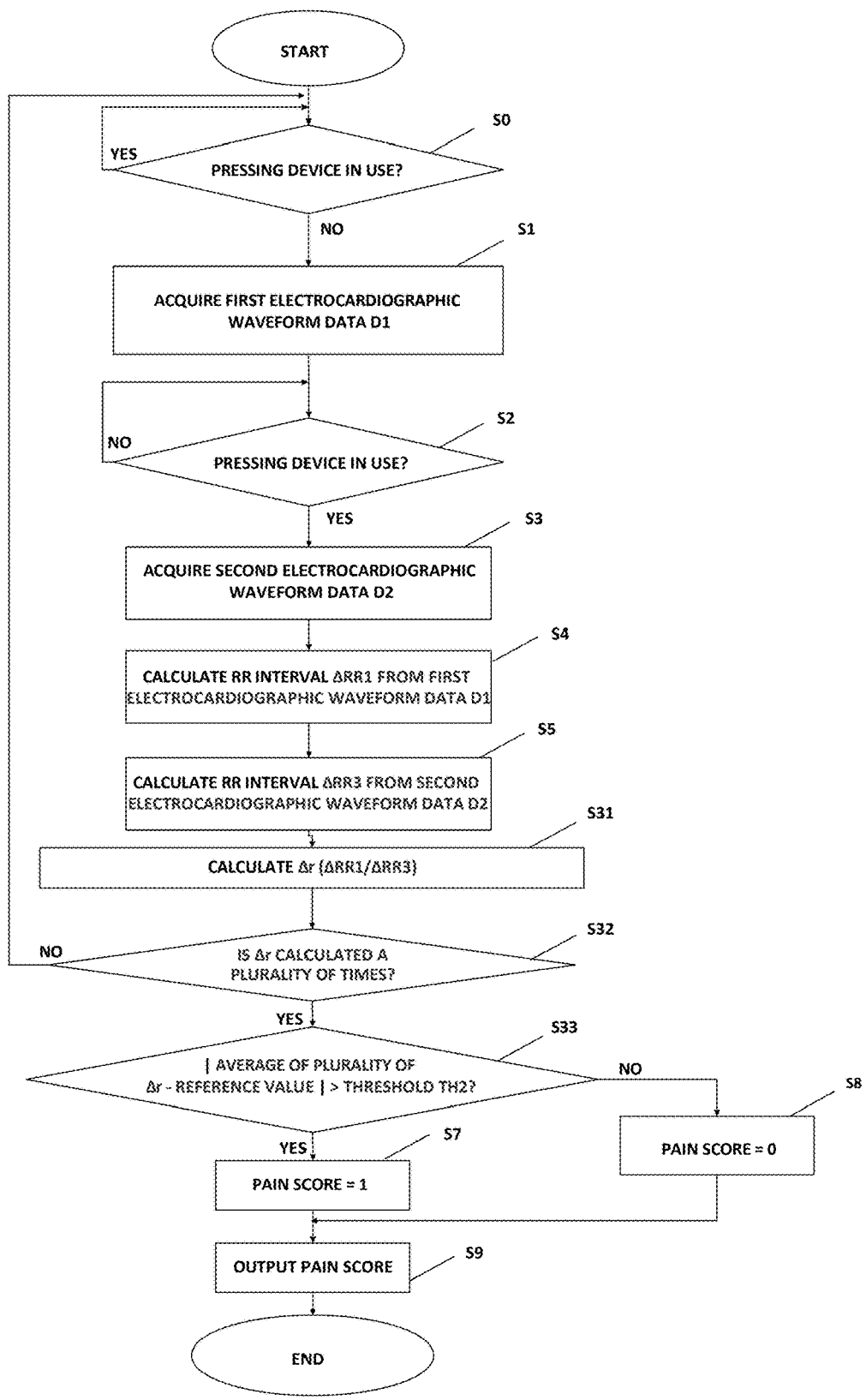
FIG. 8 is a flowchart for illustrating a third modified example of the operation of the control unit 21 of the electronic device 20 illustrated in FIG. 1.

FIG. 8 is a flowchart for illustrating a third modified example of the operation of the control unit 21 of the electronic device 20 illustrated in FIG. 1. The flowchart illustrated in FIG. 8 is identical to FIG. 5 except that step S6 is changed to step S31, step S32, and step S33. In FIG. 8, the identical processing as that in FIG. 5 is assigned with the identical reference sign and description thereof is omitted.

After step S5, the pain determination unit 21B calculates a ratio Δr (=ΔRR1/ΔRR3) between the RR interval ΔRR1 and the RR interval ΔRR3 (step S31). Thereafter, the pain determination unit 21B determines whether the ratio Δr is calculated a plurality of times (for example, twice) (step S32). When the ratio Δr is not calculated twice (step S32: NO), the pain determination unit 21B shifts the processing to step S0. When the ratio Δr is calculated twice (step S32: YES), the pain determination unit 21B calculates an average value of the two ratios Δr and determines whether an absolute value of a difference between the average value thereof and a reference value exceeds the threshold TH2 (step S33).

When the absolute value exceeds the threshold TH2 (step S33: YES), the pain determination unit 21B performs the processing of step S7. When the absolute value is at the threshold TH2 or lower (step S33: NO), the pain determination unit 21B performs the processing of step S8.

As described above, according to the operation example illustrated in FIG. 7, the degree of pain is determined based on a plurality of the ratios Δr; therefore, determination accuracy can be increased.

Additionally, in step S33 of FIG. 8, the maximum and minimum values of the plurality of ratios Δr may be excluded, and an average value of the remaining ratios Δr may be calculated and an absolute value of a difference between the average value thereof and the reference value may be compared with the threshold TH2. Alternatively, an absolute value of a difference between a median value of the plurality of ratios Δr and the reference value may be compared with the threshold TH2. As a result, the influence of sudden noise or the like can be eliminated.

Moreover, in step S33 of FIG. 8, an absolute value of a difference between each of the plurality of ratios Δr and the reference value is calculated, and of a plurality of the absolute values calculated as such, those exceeding the threshold TH2 may reach a predetermined number (one or more freely selected values). In such a case, the processing may be shifted to step S7. Of the plurality of the absolute values, those exceeding the threshold TH2 may not reach the predetermined number (one or more freely selected values). In such a case, the processing may be shifted to step S8.

In the previous description, the pain determination unit 21B compares the RR interval in a state where no load is applied to the user with the RR interval in a state where a load is applied to the user, and the degree of pain of the user is thereby determined. Alternatively, instead of the RR intervals, even when a PP interval that is an interval between P waves in the two adjacent electrocardiographic waveforms, a similar effect can be obtained by using the PP interval. Further, instead of the RR interval or the PP interval, a potential difference between the bottom of the Q wave and the peak of the R wave in the electrocardiographic waveform may be used.

Furthermore, in the above description, the dedicated pressing device 30 is used to apply a load to the user; however, a method of applying a load to the user may employ a method of, for example, pressing the affected area with a finger. By using the pressing device 30, an identical level of load can consistently be applied to the user; therefore, changes in the degree of pain can be accurately determined.

While various embodiments have been described with reference to the drawings, needless to say, the present invention is not limited to such examples. It will be apparent to those skilled in the art that various changes and modifications can be made within the scope of the claims, and it is understood that these naturally belong within the technical scope of the present invention. Further, each of the components of the above-described embodiments may be combined as desired within a range that does not depart from the spirit of the present invention.

Note that the present application is based on Japanese Patent Application filed on Mar. 13, 2019 (Japanese Patent Application No. 2019-045936), the content of which is incorporated herein by reference.

REFERENCE SIGNS LIST

100 Pain evaluation system
10 Electrocardiograph
20 Electronic device
30 Pressing device
21 Control unit
21A Electrocardiographic waveform acquisition unit
21B Pain determination unit
22 Display unit
D1 First electrocardiographic waveform data
D2 Second electrocardiographic waveform data
W1, W2, W3, W4, W5, W6 Electrocardiographic waveform

The invention claimed is:

1. A pain evaluation system for evaluating pain of a user, the pain evaluation system comprising:
a rod-shaped pressing device including a rod-shaped member configured to apply a pressing load to a body of the user, and a communication interface configured to transmit information regarding whether the pressing load is applied to the body of the user;
an electrocardiograph configured to collect a first electrocardiographic waveform data of the user in a state where the pressing load of the rod-shaped pressing device is not applied to the body of the user and collect a second electrocardiographic waveform data of the user in a state where the pressing load of the rod-shaped device is applied to the body of the user with a certain force; and
a processor configured to:
receive the information from the communication interface of the rod-shaped pressing device regarding whether the pressing load is applied to the body of the user;
acquire electrocardiographic waveform data of the user from the electrocardiograph;
compare a PP interval or a RR interval obtained from two adjacent electrocardiographic waveforms of the first electrocardiographic waveform data that are obtained in the state where the pressing load is not applied to the body of the user and a PP interval or a RR interval obtained from two adjacent electrocardiographic waveforms of the second electrocardiographic waveform data that are obtained in the state where the pressing load is applied to the body of the user with a certain force; and
determine, based on the comparison between the PP interval or the RR interval obtained from the two adjacent electrocardiographic waveforms of first electrocardiographic waveform data that are obtained in the state where the pressing load is not applied to the body of the user and the PP interval or the RR interval obtained from the two adjacent electrocardiographic waveforms of the second electrocardiographic waveform data that are obtained in the state where the pressing load is applied to the body of the user with the certain force, a degree of pain sensed by the user in the state where the pressing load is applied.

2. The pain evaluation system according to claim 1, wherein the processor is further configured to:
calculate a difference or ratio between the PP interval or the RR interval of the first electrocardiographic waveform data and the PP interval or the RR interval of the second electrocardiographic waveform data; and
determine the degree of pain based on the difference or ratio between the PP interval or the RR interval of the first electrocardiographic waveform data and the PP interval or the RR interval of the second electrocardiographic waveform data.

3. The pain evaluation system according to claim 2, wherein the processor is configured to:
calculate an absolute value of the difference;
determine whether the absolute value of the difference exceeds a threshold; and
determine the degree of pain to be larger when the absolute value exceeds the threshold as compared to when the absolute value is less than or equal to the threshold.

4. The pain evaluation system according to claim 1, wherein the processor is further configured to:
calculate an absolute value of a difference between a ratio between the PP interval or the RR interval of the first electrocardiographic waveform data and the PP interval or the RR interval of the second electrocardiographic waveform data and a reference value;

determine whether the absolute value of the difference between the ratio and the reference value exceeds a threshold; and determine that the degree of pain is larger than that when the absolute value of the difference is at the threshold or lower.

5. The pain evaluation system according to claim 2, wherein the processor is further configured to:

acquire a plurality of distinct pairs of the first electrocardiographic waveform data and the second electrocardiographic waveform data obtained at different timings; and calculate the difference for each pair of the first electrocardiographic waveform data and the second electrocardiographic waveform data that are obtained at different timings, and determine the degree of pain based on a plurality of the differences.

6. The pain evaluation system according to claim 5, wherein the processor is further configured to:

calculate an average value of absolute values of the plurality of the differences;

determine whether the average value of absolute values of the plurality of the differences exceeds a threshold; and determine that the degree of pain is larger than that when the average value is at the threshold or lower.

7. The pain evaluation system according to claim 2, wherein the processor is further configured to:

acquire a plurality of distinct pairs of the first electrocardiographic waveform data and the second electrocardiographic waveform data obtained at different timings; and calculate the ratio for each of the first electrocardiographic waveform data and the second electrocardiographic waveform data that are obtained at different timings, and determine the degree of pain based on a plurality of the ratios.

8. The pain evaluation system according to claim 7, wherein the processor is further configured to:

calculate a difference between an average value of the plurality of the ratios and a reference value; determine whether the difference between the average value of the plurality of the ratios and the reference value exceeds a threshold; and determine that the degree of pain is larger than that when the difference is at the threshold or lower.

9. The pain evaluation system according to claim 2, wherein the processor is further configured to:

calculate a plurality of the PP intervals based on the first electrocardiographic waveform data or a plurality of the RR intervals based on the first electrocardiographic waveform data, and a plurality of the PP intervals based on the second electrocardiographic waveform data or a plurality of the RR intervals based on the second electrocardiographic waveform data; and calculate, as the ratio or the difference, a ratio or difference between an average value of the plurality of the PP intervals based on the first electrocardiographic waveform data or an average value of the plurality of the RR intervals based on the first electrocardiographic waveform data, and an average value of the plurality of the PP intervals based on the second electrocardiographic waveform data or an average value of the plurality of the RR intervals based on the second electrocardiographic waveform data.

10. A pain evaluation method of evaluating pain of a user, the pain evaluation method performed in a system including a rod-shaped pressing device including a rod-shaped member configured to apply a pressing load to a body of the user and a communication interface configured to transmit information regarding whether the pressing load is applied to the body of the user; an electrocardiograph configured to collect a first electrocardiographic waveform data of the user in a state where the pressing load of the rod-shaped pressing device is not applied to the body of the user and collect a second electrocardiographic waveform data of the user in a state where the pressing load of the rod-shaped device is applied to the body of the user with a certain force; and a processor, the method comprising:

a receiving step of receiving the information from the communication interface of the rod-shaped pressing device regarding whether the pressing load is applied to the body of the user;

an electrocardiographic waveform data acquisition step of acquiring the first electrocardiographic waveform data and the second electrocardiographic waveform data of the user;

a comparing step of comparing a PP interval or a RR interval obtained from two adjacent electrocardiographic waveforms of the first electrocardiographic waveform data obtained by the electrocardiographic waveform acquisition step in a state where the pressing load is not applied to the body of the user and a PP interval or a RR interval obtained from two adjacent electrocardiographic waveforms of the second electrocardiographic waveform data obtained by the electrocardiographic waveform acquisition step in a state where the pressing load is applied to the body of the user with a certain force; and a pain determination step of determining, based on the comparing step of comparing the PP interval or the RR interval obtained from two adjacent electrocardiographic waveforms of first electrocardiographic waveform data obtained by the electrocardiographic waveform acquisition step in the state where a pressing load is not applied to the body of the user and the PP interval or the RR interval obtained from two adjacent electrocardiographic waveforms of second electrocardiographic waveform data obtained by the electrocardiographic waveform acquisition step in the where the pressing load is applied to the body of the user with the certain force, a degree of pain sensed by the user in the state where the pressing load is applied.

11. A non-transitory storage medium storing a pain evaluation program for evaluating pain of a user, the program allowing a computer to execute, in a system including a rod-shaped pressing device including a rod-shaped member configured to apply a pressing load to a body of the user and a communication interface configured to transmit information regarding whether the pressing load is applied to the body of the user; an electrocardiograph configured to collect a first electrocardiographic waveform data of the user in a state where the pressing load of the rod-shaped pressing device is not applied to the body of the user and collect a second electrocardiographic waveform data of the user in a state where the pressing load of the rod-shaped device is applied to the body of the user with a certain force; and a processor, the following:

a receiving step of receiving the information from the communication interface of the rod-shaped pressing device regarding whether the pressing load is applied to the body of the user;

an electrocardiographic waveform data acquisition step of acquiring the first electrocardiographic waveform data and the second electrocardiographic waveform data of the user;

a comparing step of comparing a PP interval or a RR interval obtained from two adjacent electrocardiographic waveforms of the first electrocardiographic waveform data obtained by the electrocardiographic waveform acquisition step in a state where the pressing load is not applied to the body of the user and a PP interval or a RR interval obtained from two adjacent electrocardiographic waveforms of the second electrocardiographic waveform data obtained by the electrocardiographic waveform acquisition step in a state where the pressing load is applied to the body of the user with a certain force, and a pain determination step of determining, based on the comparing step comparing the PP interval or the RR interval obtained from two adjacent electrocardiographic waveforms of first electrocardiographic waveform data obtained by the electrocardiographic waveform acquisition step in the state where the pressing load is not applied to the body of the user and the PP interval or the RR interval obtained from two adjacent electrocardiographic waveforms of second electrocardiographic waveform data obtained by the electrocardiographic waveform acquisition step in the state where the pressing load is applied to the body of the user with the certain force, a degree of pain sensed by the user in the state where the pressing load is applied.

* * * * *